United States Patent
Crump et al.

(10) Patent No.: US 9,343,873 B2
(45) Date of Patent: May 17, 2016

(54) LASER DIODE WITH HIGH EFFICIENCY

(75) Inventors: Paul Crump, Berlin (DE); Goetz Erbert, Loebau (DE); Hans Wenzel, Berlin (DE)

(73) Assignee: Forschungsverbund Berlin E.V., Berlin (DE)

(*) Notice: Subject to any disclaimer, the term of this patent is extended or adjusted under 35 U.S.C. 154(b) by 1 day.

(21) Appl. No.: 13/823,277

(22) PCT Filed: Sep. 12, 2011

(86) PCT No.: PCT/EP2011/065751
§ 371 (c)(1),
(2), (4) Date: Apr. 24, 2013

(87) PCT Pub. No.: WO2012/034972
PCT Pub. Date: Mar. 22, 2012

(65) Prior Publication Data
US 2013/0208748 A1    Aug. 15, 2013

(30) Foreign Application Priority Data
Sep. 14, 2010   (DE) .................. 10 2010 040 767

(51) Int. Cl.
*H01S 5/00* (2006.01)
*H01S 5/20* (2006.01)
(Continued)

(52) U.S. Cl.
CPC ... *H01S 5/20* (2013.01); *H01S 5/22* (2013.01); *A61B 18/203* (2013.01);
(Continued)

(58) Field of Classification Search
CPC ........ H01S 5/2031; H01S 5/2202; H01S 5/22
See application file for complete search history.

(56) References Cited

U.S. PATENT DOCUMENTS 4,328,469 A    5/1982   Scifres et al.
4,989,213 A *  1/1991   Haw et al. .................. 372/45.01
(Continued)

FOREIGN PATENT DOCUMENTS

| EP | 1460741 | 9/2004 |
|---|---|---|
| WO | WO 01/57974 | 8/2001 |
| WO | WO 2012/034972 | 3/2012 |

OTHER PUBLICATIONS

International Search Report Dated Jun. 27, 2012 From the International Searching Authority Re. Application No. PCT/EP2011/065751.

(Continued)

*Primary Examiner* — Jessica Stultz
*Assistant Examiner* — Sean Hagan

(57) ABSTRACT

It is the object of the present invention to specify a light source with high efficiency and high eye safety at the same time.
For this purpose, the active layer (10), the first cladding layer (14), the first waveguide layer (12), the second waveguide layer (16), and the second cladding layer (18) should be designed such that $0.01\ \mu m \leq d_{wL} \leq 1.0\ \mu m$ and $\Delta n \geq 0.04$, where $d_{wL}$ is the sum total of the layer thickness of the first waveguide layer (12), the layer thickness of the active layer (10), and the layer thickness of the second waveguide layer (16) and $\Delta n$ is a maximum of the refractive index difference between the first cladding layer (14) and the first waveguide layer (12) and the refractive index difference between the second waveguide layer (16) and the second cladding layer (18).

14 Claims, 10 Drawing Sheets

(51) Int. Cl.
  *H01S 5/22*  (2006.01)
  *A61B 18/20*  (2006.01)
  *A61B 18/00*  (2006.01)
  *A61B 19/00*  (2006.01)
  *H01S 5/32*  (2006.01)

(52) U.S. Cl.
  CPC  *A61B 2018/00476* (2013.01); *A61B 2019/409* (2013.01); *H01S 5/2031* (2013.01); *H01S 5/3213* (2013.01); *H01S 2301/185* (2013.01)

(56) References Cited

U.S. PATENT DOCUMENTS

| | | |
|---|---|---|
| 6,172,998 B1 | 1/2001 | Horie et al. |
| 6,430,202 B1* | 8/2002 | Van de Walle et al. .... 372/45.01 |
| 6,650,671 B1* | 11/2003 | Garbuzov et al. .......... 372/45.01 |
| 6,711,191 B1* | 3/2004 | Kozaki et al. ............... 372/43.01 |
| 6,731,663 B1 | 5/2004 | Kasukawa et al. |
| 7,118,563 B2* | 10/2006 | Weckwerth et al. ............... 606/9 |
| 2002/0024984 A1* | 2/2002 | Ohkubo et al. ................. 372/46 |
| 2003/0179794 A1 | 9/2003 | Mihashi et al. |
| 2004/0017836 A1* | 1/2004 | Buda et al. ...................... 372/45 |
| 2004/0066818 A1 | 4/2004 | Yamamoto et al. |
| 2004/0184497 A1* | 9/2004 | Kneissl et al. ................. 372/45 |
| 2008/0036044 A1 | 2/2008 | Sakuma et al. |
| 2008/0117945 A1 | 5/2008 | Kuramoto |
| 2010/0150196 A1 | 6/2010 | Rossin |
| 2010/0290496 A1* | 11/2010 | Takayama et al. ....... 372/46.012 |

OTHER PUBLICATIONS

Ryvkin et al. "Nonbroadened Asymmetric Waveguide Diode Lasers Promise Much Narrower Far Fields Than Broadened Symmetric Waveguide Ones", Journal of Applied Physics, 98: 026107-1-026107-2, 2002.

Shigihara et al. "High-Power 980-NM Ridge Waveguide Laser Diodes Including an Asymmetrically Expanded Optical Field Normal to the Active Layer", IEEE Journal of Quantum Electronics, XP011065253, 38(8): 1081-1088, Aug. 2002. Abstract, Fig.1.

* cited by examiner

LASER DIODE WITH HIGH EFFICIENCY

RELATED APPLICATIONS

This application is a National Phase of PCT Patent Application No. PCT/EP2011/065751 having International filing date of Sep. 12, 2011, which claims the benefit of German Patent Application No. 10 2010 040 767.4 filed on Sep. 14, 2010. The contents of the above applications are all incorporated by reference as if fully set forth herein in their entirety.

FIELD AND BACKGROUND OF THE INVENTION

The present invention relates to a laser diode with high efficiency and high eye safety.

Efficient light sources are in demand in many fields of application, such as cosmetics (hair removal), lighting, or data transmission, but these light sources must provide high eye safety to reliably exclude harm to health due to undesirable irradiance incident on the human eye.

SUMMARY OF THE INVENTION

In the fields of application mentioned, flash lights or superluminescent diodes are used, but these have a rather low efficiency. While laser diodes are highly efficient, they do not provide the required level of eye safety for many applications. An effort to overcome these disadvantages is known from U.S. Pat. No. 7,118,563 B2 that proposes to combine laser diodes with a high efficiency and concave lenses or diffusers. While eye safety can be enhanced in this way, efficiency is disadvantageously reduced. Increased cost and complicated assembly are further disadvantages.

The object of the present invention is to specify a light source with high efficiency and high eye safety at the same time. In addition, the light source according to the invention should be inexpensive to manufacture and easy to assemble.

These objects are achieved by the characteristics defined in claim 1. Useful embodiments of the invention are described in the dependent claims.

The inventive idea is to design the waveguiding in a laser diode such that the far-field divergence (95% angle) is more than 50°, more preferably more than 70° in the vertical direction (fast axis) and/or in the lateral direction (slow axis). It is preferred that the laser diode is designed such that the far-field divergence is more than 50°, more preferably more than 70°, both in the vertical direction and in the lateral direction.

In this way, eye safety can be ensured at a specific distance depending on the laser output without an extra effort (lenses, diffusers). Far-field divergence is that vertical and/or lateral angle at a distance of more than 1 mm from the emission facet in which 95% of the radiation output are included or emitted, respectively.

The optoelectronic semiconductor element (laser diode) of the invention comprises an active layer that is suitable for generating radiation, wherein a first waveguide layer is provided on a first side of the active layer, a first cladding layer is provided on the first waveguide layer, a second waveguide layer is provided on a second side of the active layer, and a second cladding layer is provided on the second waveguide layer, wherein the first and the second side are opposite one another relative to the active layer, wherein a reflection facet for reflecting the radiation emitted from the active layer and an emission facet for partial reflection and partial feed-out of the radiation emitted from the active layer are provided, wherein said reflection facet and said emission facet are each provided in the marginal area of the active layer and arranged opposite one another relative to the active layer, wherein, in order to increase the vertical far-field divergence, the active layer, the first cladding layer, the first waveguide layer, the second waveguide layer, and the second cladding layer are designed such that the conditions $0.01\ \mu m \leq d_{wL} \leq 1.0\ \mu m$ and $\Delta n \geq 0.04$ are met, where $d_{wL}$ is the sum total of the layer thickness of the first waveguide layer, the layer thickness of the active layer, and the layer thickness of the second waveguide layer, and $\Delta n$ is a maximum of the refractive index difference between the first cladding layer and the first waveguide layer, and the refractive index difference between the second waveguide layer and the second cladding layer.

It was found that the (vertical) far-field divergence is greater than 70° for a (vertical) layer structure and that the radiation emitted is eye safe in the meaning of this invention if the sum total of the layer thicknesses of the waveguides and the active layer is suitably selected and if the (maximum) refractive-index difference between waveguide layers and the associated cladding layers exceeds a specific value. Conventional designs of laser diodes are aimed at keeping the (vertical and lateral) far-field divergences as low as possible to be able to focus the laser radiation properly. Contrary to the conventional approach, it was found that a laser diode with a high (vertical) far-field divergence (greater than 50°, more preferably greater than 70°) offers both high efficiency and high eye safety. Therefore, the laser diode according to the invention is especially suited for applications that require high efficiency on the one hand and high eye safety on the other, such as cosmetic treatments.

It s preferred that the first cladding layer, the first waveguide layer, the second waveguide layer, and the second cladding layer are designed such that the condition $\Delta n > 0.1$, more preferably $\Delta n > 0.15$, more preferably $\Delta n > 0.20$, more preferably $\Delta n > 0.25$ and more preferably $\Delta n > 0.30$ is met. The (vertical) far-field divergence may be further increased, according to the invention, by a higher refractive index difference between the waveguide layer and the cladding layer. It is preferred that the refractive indices of the first and second waveguide layers are the same. It is preferred that the refractive indices of the first and second cladding layers are the same. The refractive index refers to the central wavelength of the radiation emitted by the active layer. The central wavelength of the radiation emitted by the active layer is preferably in the range from 380 nm to 10 µm, more preferably from 380 nm to 2000 nm.

It is preferred that the first waveguide layer, the active layer, and the second waveguide layer are designed such that the condition $0.01\ \mu m \leq d_{wL} \leq 0.75\ \mu m$, preferably $0.01\ \mu m \leq d_{wL} \leq 0.5\ \mu m$, and more preferably $0.01\ \mu m \leq d_{wL} \leq 0.3\ \mu m$ is met. The values for $d_{wL}$ mentioned above are preferably suited for a (hair removal) laser that emits at 800 nm.

The layer thickness limits for structures with another emission wavelength vary in scale with the internal wavelength of the respective material. It was found that the (vertical) far-field divergence and thus the eye safety can be further increased, especially for the fields indicated.

It is preferred that the active layer stretches across the entire area between the reflection face and the emission facet. It is preferred that the active layer is in direct contact with the reflection facet and the emission facet.

A ridge waveguide is provided for further increasing the lateral far-field divergence, said ridge waveguide having an effective index step $\Delta n_{eff} > 0.06$, preferably an effective index step $\Delta n_{eff} > 0.10$. The effective index leap is the difference between the effective refractive index in the region of the ridge waveguide and the effective refractive index in the region next to the ridge waveguide. The so-called effective index method for determining the effective refractive index is known, for example, from Coldren and Corzine, "Diode lasers and photonic integrated circuits", Wiley-Interscience, New York, 1995, pp. 428-440, Appendix 3 ("Introduction to Optical Waveguide in Simple Double-Heterostructures").

It is preferred that the laser diode according to the invention comprises both a ridge waveguide with an effective index step $\Delta n_{eff} > 0.06$, preferably with an effective index step $\Delta n_{eff} > 0.10$ and layers (cladding layers, waveguide layers, and active layer) that meet the conditions of 0.01 µm≤$d_{wL}$≤1.0 µm and $\Delta n \geq 0.04$ (preferably a an emission wavelength of the laser of 800 nm—for applications with $\lambda \neq 800$ nm, it is preferred that the $d_{wL}$ is scaled depending on the internal wavelength in the material). A respective effective index step $\Delta n_{eff}$ can be achieved using several methods, such as etching and overgrowth, diffusion, implantation, or ridge waveguide techniques.

Use of a ridge waveguide is explained in detail here as a preferred embodiment, however the invention is not limited to it.

It is preferred that the ridge waveguide is formed by (two) grooves that are introduced (preferably etched) into the second waveguide layer and the second cladding layer (and layers above these, if any), wherein the depth of the grooves is such that a minimum distance between the side of the active layer facing the second waveguide layer and the side of the grooves facing the active layer is greater than 100 nm. In other words, the waveguide that is on top viewed from the substrate is preferably etched into as deeply as possible but not all the way through into the active layer. This increases the reliability of the component. It is particularly preferred to use an asymmetrical (preferably p-type) waveguide lying on top that comprises a great thickness compared to the other (n-type) waveguide. One advantage is that the waveguide lying on top can be etched into very deeply (very deep grooves) without etching all the way through to the active layer such that a high effective index step and therefore a high lateral far-field divergence can be achieved. On the other hand, the asymmetrical waveguide ensures great reliability because only a small portion of the radiation output is located in the active layer, which prevents a COMD (catastrophic optical mirror damage).

It is preferred that the first cladding layer and the first waveguide layer are n-type and the second waveguide layer and the second cladding layer are p-type. It is preferred that the first waveguide layer, the active layer, and the second waveguide layer are designed such that the ratio between the layer thickness of the second waveguide layer and the sum total of the layer thicknesses of the first waveguide layer, the active layer and the second waveguide layer is greater than 0.45, more preferred greater than 0.5, more preferably greater than 0.55, more preferably greater than 0.60, more preferably greater than 0.65, more preferably greater than 0.70, more preferably greater than 0.75, more preferably greater than 0.80, more preferably greater than 0.85, and more preferably greater than 0.9. It was found that a large ratio of the (preferably p-type) waveguide thickness to the overall thickness of active layer and waveguides results in a great effective index step $\Delta n_{eff}$ and an accordingly great far-field divergence.

It is preferred that the grooves are brought close to the active layer but do not penetrate the active layer. It is preferred that a minimum distance between the side of the active layer facing the second waveguide layer and the side of the grooves facing the active layer is smaller than 500 nm, more preferably smaller than 250 nm.

The right selection of the width of the ridge waveguide is a balance between diverse effects. First, ridge waveguides that can be feasibly produced have a width>1 µm due to process tolerances. Wide ridge waveguides carry more than one lateral wave mode. Higher-order modes have wider lateral angles and are preferred for high eye safety and large illumination volumes. But not every upper mode plays a role in laser operation, typically only the first few modes. Structures with very large ridge waveguide widths>>50 µm produce many upper modes but the first few modes that are critical for laser operation have relatively narrow output angle. The above-mentioned vertical layer thicknesses result in a preferred lateral far-field divergence, i.e. the laser diodes with lateral output angles>70° (FF95%, far-field divergence in which 95% of the radiation energy are included).

Preferred widths of the ridge waveguide are $d_{well}$=1-20 µm, more preferably $d_{well}$=2-10 µm, and more preferably $d_{well}$=3-7 µm. It is preferred for applications with $\lambda \neq 800$ nm to scale this width with the internal wavelength in the material.

The component preferably comprises neither a diffuser nor a concave lens. It s preferred that all layers (especially the active layer, waveguide layers, and cladding layers) have a relatively uniform layer thickness along their overall length, the ratio of maximum layer thickness to minimum layer thickness being smaller than 2. It is preferred that all layers (especially the active layer, waveguide layers, and cladding layers) have a uniform layer thickness.

BRIEF DESCRIPTION OF THE DRAWINGS

The invention is explained in greater detail with reference to embodiments. Wherein.

DESCRIPTION OF SPECIFIC EMBODIMENTS OF THE INVENTION

Figure 1A:
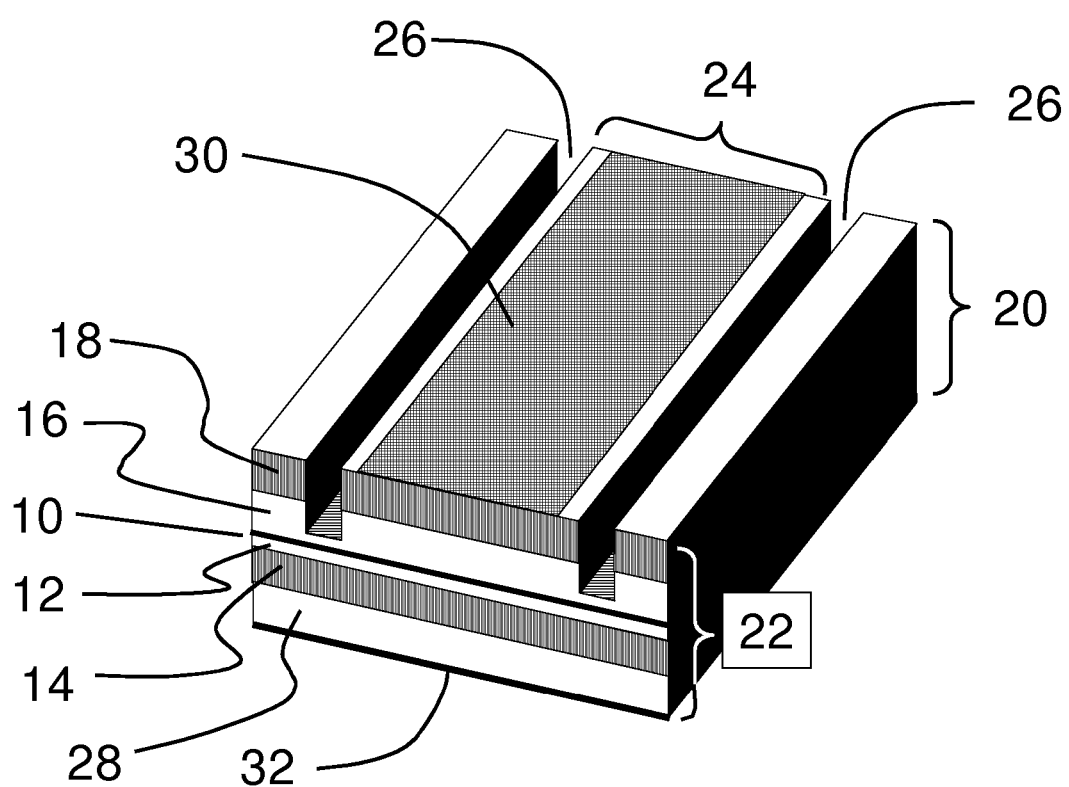
FIG. 1A shows a diagrammatic perspective view of the laser diode according to the invention.
Figure 1B:
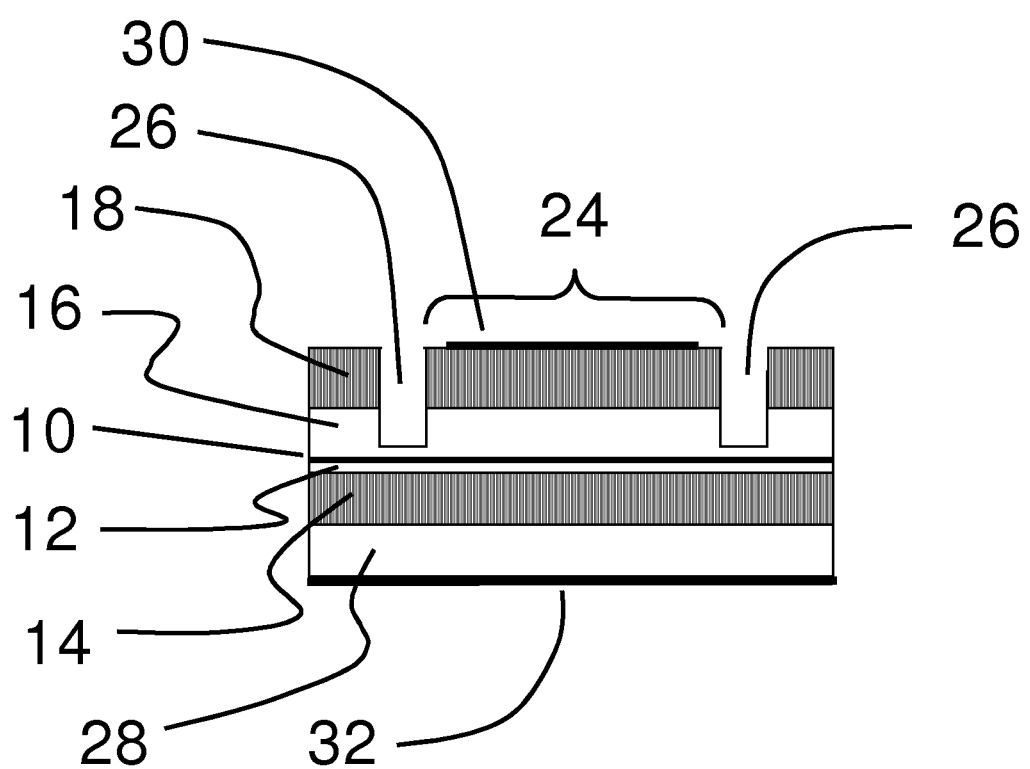
FIG. 1B shows a diagrammatic sectional view of the laser diode according to the invention from FIG. 1A along an axis transverse to the direction of light propagation.
Figure 1C:
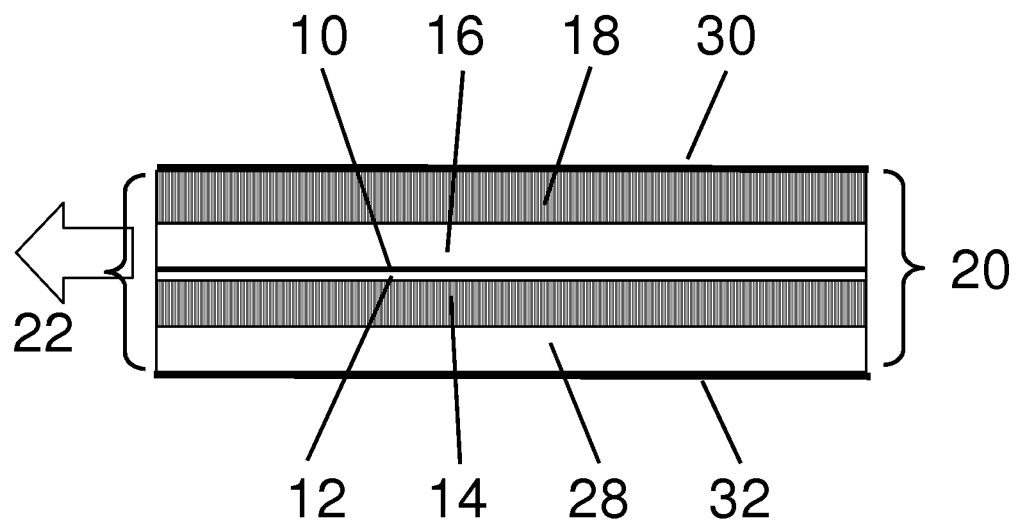
FIG. 1C shows a diagrammatic sectional view of the laser diode according to the invention from FIG. 1A along an axis parallel to the direction of light propagation.

FIGS. 1A-1C show perspective and sectional views of the laser diode according to the invention.

The laser diode according to the invention comprises a vertical layer structure with a substrate 28, a first n-type cladding layer 14 located on top thereof, a first n-type waveguide layer 12 located on top thereof, an active layer 10 located on top thereof, a second p-type waveguide layer 16 located on top thereof, and a second p-type cladding layer 18 located on top thereof.

Furthermore, the laser diode of the invention on its lateral opposite ends comprises a reflection facet 20 with high reflectivity for the central wavelength of the radiation emitted by the active layer 10 and an emission facet 22 with a reflectivity that facilitates feed-out of the radiation. It is preferred that the reflectivity of the reflection facet 20 is greater than 0.8, more preferably greater than 0.9, and more preferably greater than 0.99. The reflectivity of the emission facet 22 is smaller than the reflectivity of the reflection facet 20.

The laser diode of the invention further comprises contacts 30 and 32 for injecting charge carriers. In a structure formed in this way, charge carriers of a first polarity can enter the active layer 10 via the first contact 30, the first cladding layer 14 (preferably n-type in this embodiment), and the first waveguide layer (preferably n-type in this embodiment), and charge carriers of the opposite polarity can also enter the active layer 10 via the second contact 32, the second cladding layer 18 (preferably p-type in this embodiment), and the second waveguide layer 16 (preferably p-type in this embodiment) and recombine there, which causes an emission. The facets 20 and 22 thus form a cavity to achieve laser operation.

The detailed structure of the preferred embodiment shown in FIGS. 1A-1C is a diode laser with an active layer 10 having an emission wavelength at 808 nm, made of AlGaAs and comprising a GaAsP single quantum well. The cladding and waveguide layers 12, 14, 16, 18 are made of Al(x)Ga(1-x)As. For the waveguides 12, 16, the x in Al(x)Ga(1-x)As preferably is between 85% and 20%, more preferably between 70% and 25%, and more preferably between 50% and 30%.

To meet the Δn target, x for the cladding layers 14, 18 in Al(x)Ga(1-x)As is preferably >+5% compared to the aluminum content of the waveguide layers 12, 16, more preferably >+10%, more preferably >+25%, and more preferably >+50% (but max. 100%). The preferred thickness of the waveguide 24 is 0.01-1.0 μm; more preferably 0.05-0.7 μm and even more preferably 0.1-0.5 μm. The ratio of the thickness of the top waveguide 16 (p-type here) to the thickness of the bottom waveguide 12 (n-type here) preferably is >65%, more preferably >75% and even more preferably >85%. It is preferred that the etching depth of the ridge waveguide 24 is selected such that the etched area is 100 nm away from the active layer 10 (along a vertical axis). It is preferred that the width of the ridge waveguide 24 is 1-24 μm, more preferred 2-10 μm, and even more preferred 3-7 μm.

Figure 2:
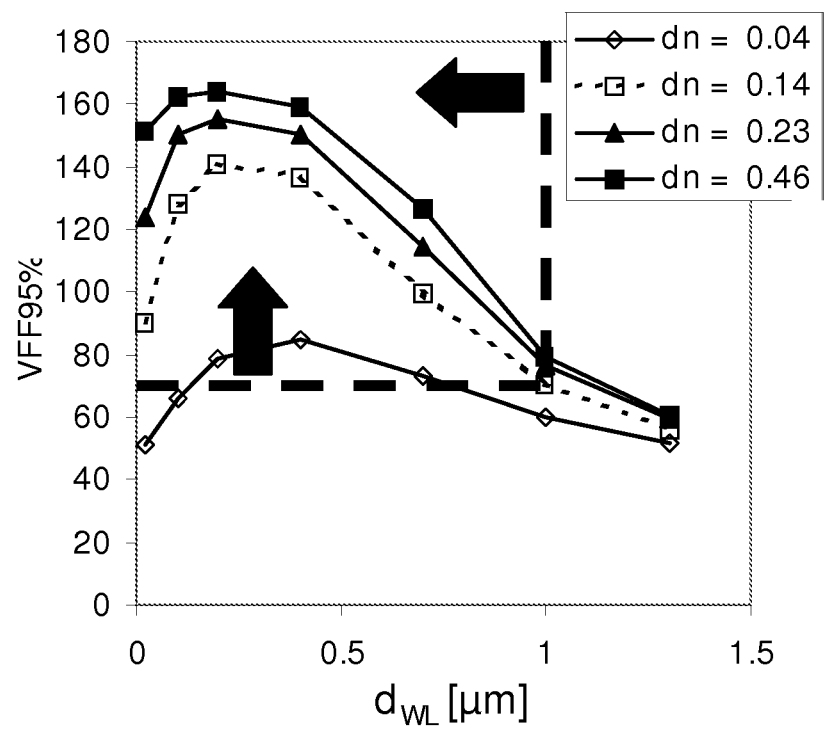
FIG. 2 shows the dependence of the vertical far-field divergence of the laser diode according to the invention on the overall thickness of the waveguide layers including the active layer on the one hand and the refractive index difference between waveguide layers and cladding layers on the other.

FIG. 2 shows the dependence of the vertical far-field divergence (VFF95%, vertical far-field divergence which includes 95% of the vertical radiation energy) of the laser diode of FIG. 1 on the overall thickness $d_{wL}$ that results from the sum total of the first waveguide layer 12, the active layer 10, and the second waveguide layer 16. The dependence is shown for different refractive index differences Δn between the first cladding layer 14 and the first waveguide layer 12. In this embodiment, the refractive index difference Δn between the first cladding layer 14 and the first waveguide layer 12 is equal to the refractive index difference between the second cladding layer 18 and the second waveguide layer 16. It can be seen that a sufficient vertical far-field divergence for an overall thickness $d_{wL}$ between 0.01 μm≤$d_{wL}$≤1.0 μm and a refractive index difference for Δn (or Δn, respectively)≥0.04 (or Δn, respectively) can be achieved. Particularly high far-field divergences can be achieved for an overall thickness $d_{wL}$ between 0.01 μm≤$d_{wL}$≤0.5 μm and a refractive index difference for Δn (or Δn, respectively)≥0.2.

Figure 3:
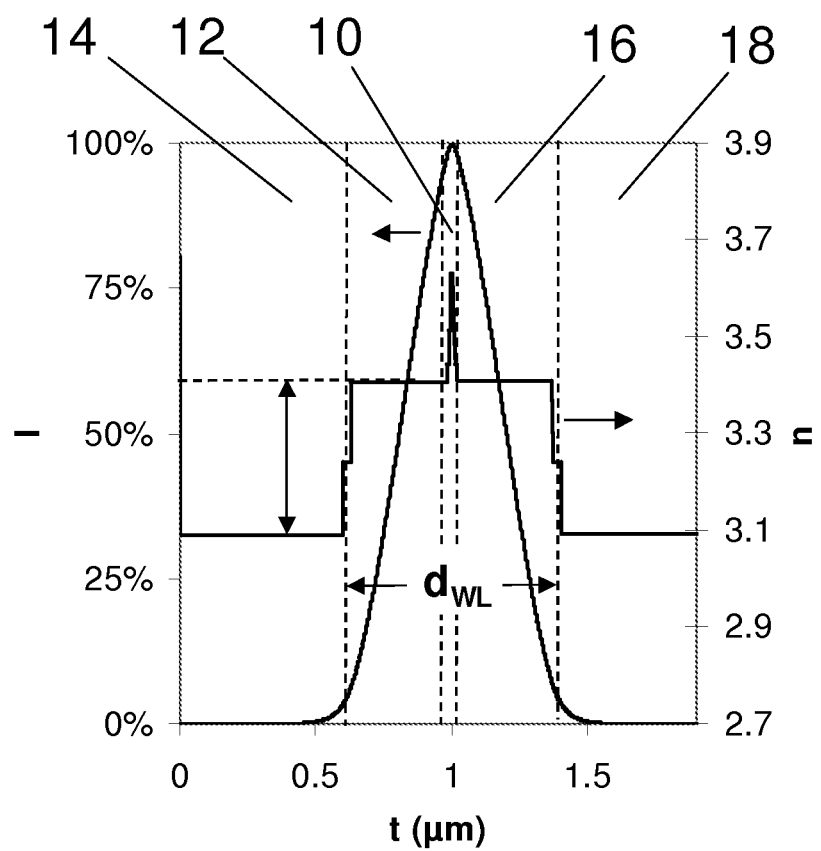
FIG. 3 shows the refractive index distribution along the layers of the laser diode of the invention with symmetrical waveguide layers and the associated vertical distribution of mode intensity in the laser diode of the invention.

FIG. 3 shows the refractive index distribution (refractive index n) along the layers 10, 12, 14, 16, and 18 along a vertical axis with symmetrical waveguide layers (layer thickness 12=layer thickness 16) and the associated vertical distribution of the mode intensity I. The exact vertical position (depth) of each layer 10, 12, 14, 16, and 18 on the vertical axis is referenced by t. FIG. 3 also shows the refractive index difference (Δn) between the layers 12 and 14 as well as 16 and 18, and the overall thickness $d_{wL}$.

Figure 4:
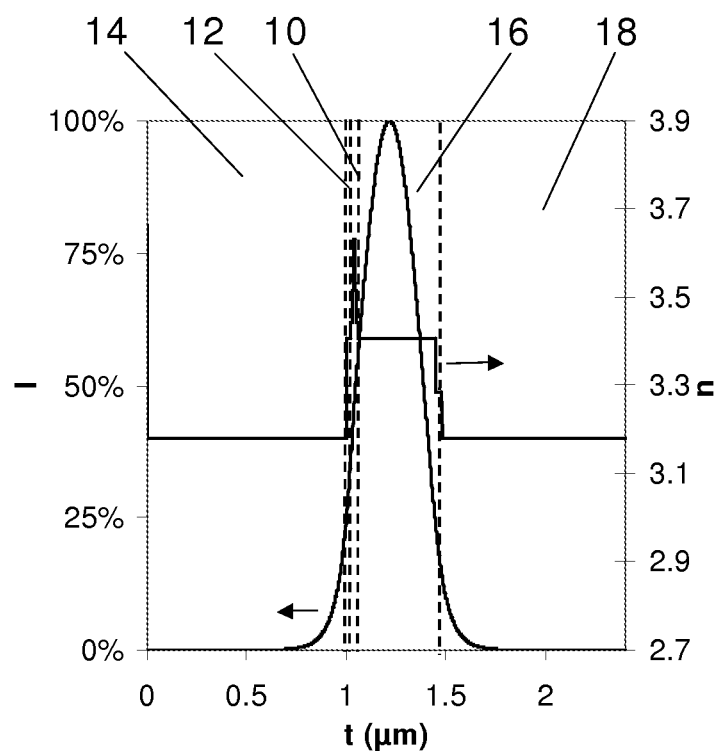
FIG. 4 shows the refractive index distribution along the layers of the laser diode of the invention with asymmetrical waveguide layers and the associated vertical distribution of mode intensity in the laser diode of the invention.

FIG. 4, like FIG. 3, shows the refractive index distribution as well as the associated vertical distribution of the mode intensity I for asymmetrical waveguide layers, where the thickness of the first waveguide layer 12 is considerably less than the thickness of the second waveguide layer 16. As can be seen from FIG. 4, the energy portion in the active layer can be reduced in this way, which advantageously prevents a COMD despite the high output of the laser diode.

Figure 5:
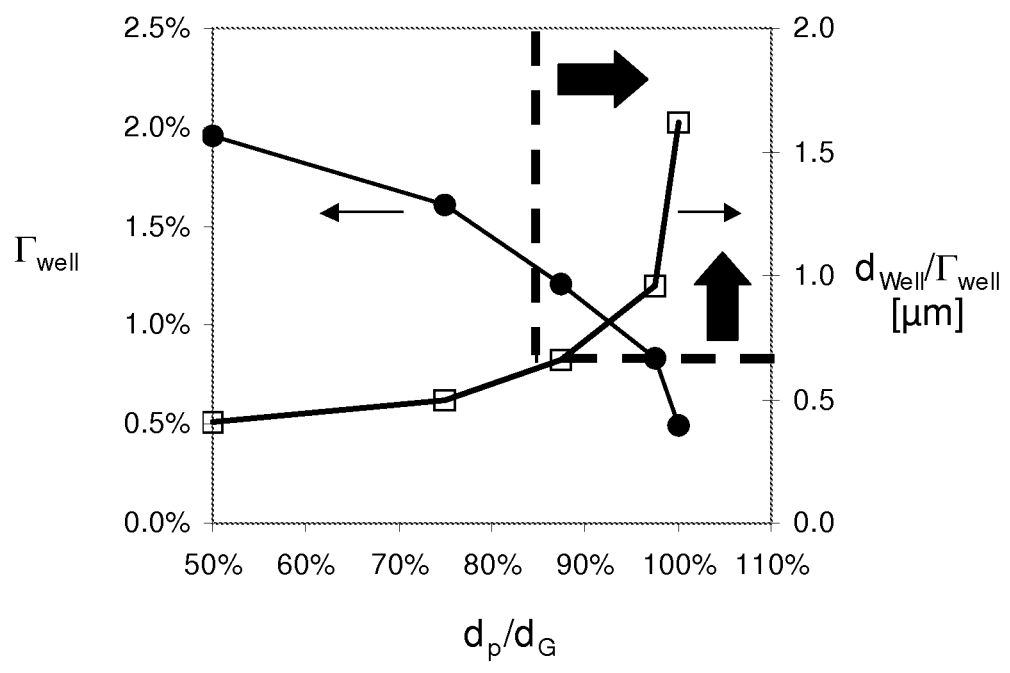
FIG. 5 shows the dependence of the proportion of radiation energy contained in the active layer relative to the overall radiation energy on the ratio of the p-type waveguide layer thickness to the overall thickness of the waveguide layers including the active layer on the one hand, and the dependence of the ratio of active layer thickness to the proportion of radiation energy contained in the active layer on the ratio of the p-type waveguide layer thickness to the overall thickness of the waveguide layers including the active layer on the other hand.

FIG. 5 on the one hand shows the dependence of the portion of radiation energy $\Gamma_{WELL}$ present in the active layer 10 in relation to the overall radiation energy on the ratio of the p-type waveguide layer thickness $d_P$ (=layer thickness of the second waveguide layer 16) to the overall thickness $d_G$ of the waveguide layers 12, 16 including the active layer 10. In other words, the proportional radiation energy $\Gamma_{WELL}$ represents the ratio of radiation energy in the active layer 10 to the radiation energy in the entire component. It can be seen from FIG. 5 that the proportional radiation energy $\Gamma_{WELL}$ drops at an increasing $d_P/d_G$ ratio. In addition, FIG. 5 shows the dependence of the ratio of the layer thickness d of the active layer 10 to the portion of radiation energy $\Gamma_{WELL}$ in the active layer 10 on the $d_P/d_G$ ratio of the p-type waveguide layer thickness (layer thickness of 16) to the overall thickness of the waveguide layers including the active layer (sum total of the layer thicknesses of 12, 10, 16). It can be seen from FIG. 5 that the $d/\Gamma_{WELL}$ ratio drops with an increasing $d_P/d_G$ ratio.

Figure 6:
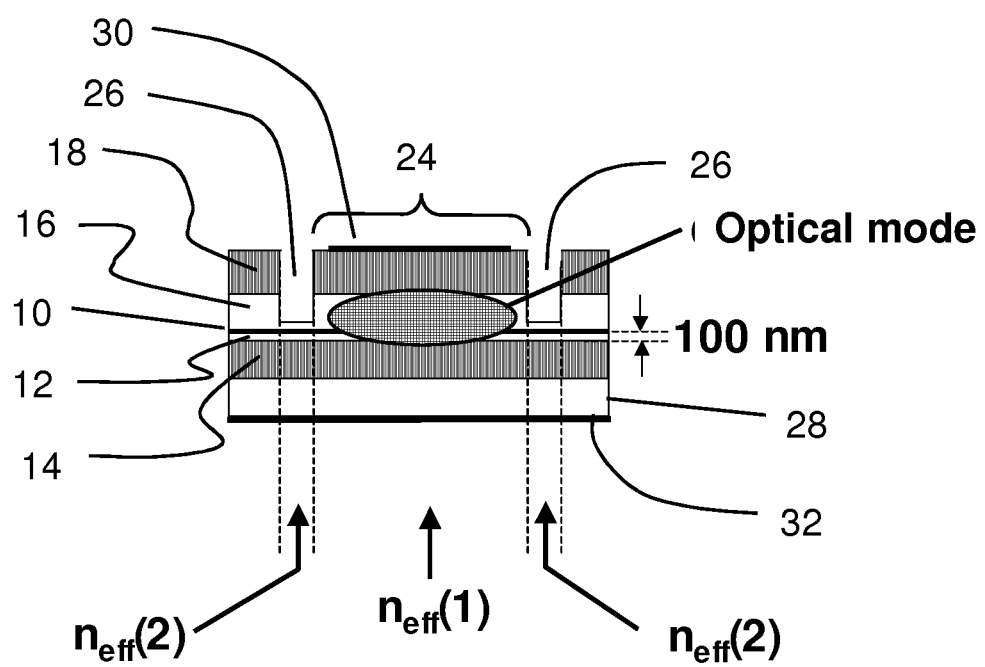
FIG. 6 shows a schematic sectional view of a preferred embodiment of a laser diode according to the invention with ridge waveguide.

FIG. 6 shows a schematic sectional view of a preferred embodiment of a laser diode according to the invention with ridge waveguide 24. The ridge waveguide 24 produces a lateral index step $\Delta n_{eff}$. The lateral index step $\Delta n_{eff}$ can be determined using the so-called effective index method for determining the effective refractive indices $n_{eff}(1)$ and $n_{eff}(2)$. The grooves 26 should be as deep as possible to increase the lateral far-field divergence, but they should not be etched into the active layer 10 to improve the stability of the component. It is preferred that a distance of at least 100 nm remains between the grooves 26 and the active layer 10. The materials of the layers 16 and 18 and the dimensions if the ridge waveguide 24 (and the grooves 28) are selected such that a sufficiently high lateral index step $\Delta n_{eff}$ and thus a sufficiently high lateral far-field divergence are achieved.

Figure 7:
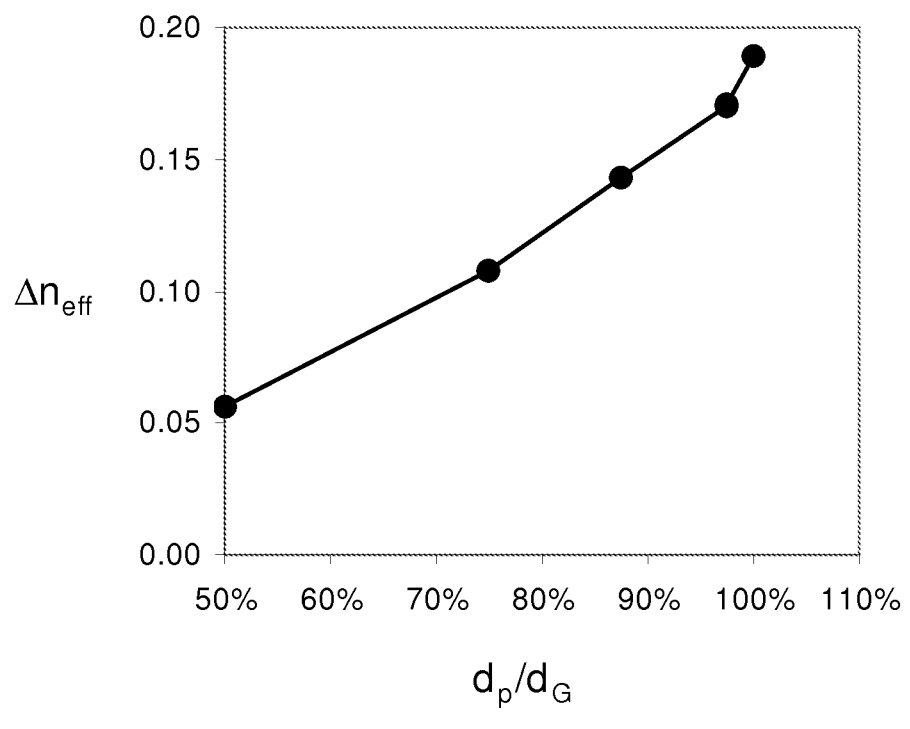
FIG. 7 shows the dependence of the effective index step $\Delta n_{eff}$ on the ratio of the p-type waveguide layer thickness to the overall thickness of the waveguide layers including the active layer.

FIG. 7 shows the dependence of the effective index step $\Delta n_{eff}$ on the $d_P/d_G$ ratio of the p-type waveguide layer thickness (layer thickness of 16) to the overall thickness of the waveguide layers including the active layer (sum total of the layer thicknesses of 12, 10, 16). It can be seen that a sufficiently high index step $\Delta n_{eff}$ can be achieved at a $d_P/d_G$ ratio greater than 0.65 (or 65%, respectively).

Figure 8:
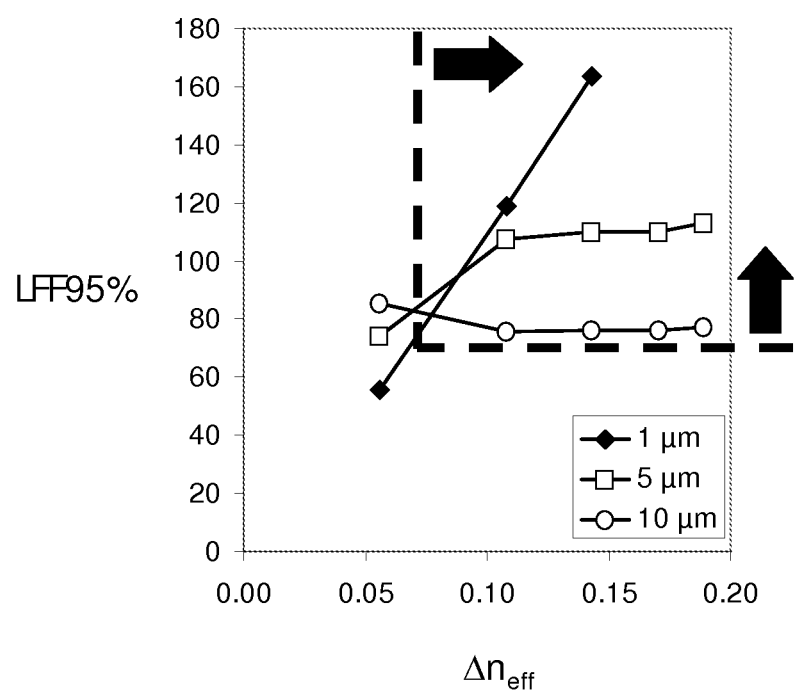
FIG. 8 shows the dependence of the vertical far-field divergence on the effective index step $\Delta n_{eff}$ on the one hand and the width of the ridge waveguide on the other.

FIG. 8 shows the dependence of the lateral far-field divergence (LFF95%, lateral far-field divergence that includes 95% of the lateral radiation energy) on the effective index step $\Delta n_{eff}$ on the one hand and the width of the ridge waveguide 24 on the other. It can be seen that a sufficiently high lateral far-field divergence for widths of the ridge waveguide 24 smaller than 10 μm, preferably smaller than 5 μm, and an effective index step $\Delta n_{eff}$ greater than 0.07 can be achieved.

The invention claimed is:

1. An optoelectronic semiconductor component, comprising:
an active layer that is suitable for generating radiation, a first waveguide layer positioned on a first side of the active layer, a first cladding layer positioned on the first waveguide layer, a second waveguide layer positioned on a second side of the active layer, and a second cladding layer positioned on the second waveguide layer, wherein the first side and the second side are opposite with respect to the active layer, wherein a reflection facet for reflecting the radiation emitted by the active layer and an emission facet for reflection and feed-out of the radiation emitted by the active layer, wherein the reflection facet and the emission facet are each positioned in the marginal area of the active layer, and wherein the reflection facet and the emission facet are positioned opposite one another with respect to the active layer, wherein:
the conditions (i) and (ii) are met:
(i) the active layer, the first cladding layer, the first waveguide layer, the second waveguide layer, and the second cladding layer are designed such that
the conditions
0.01 μm≤dwL≤1.0 μm and $\Delta n \geq 0.04$;
are met;
where dwL is the sum total of the layer thickness of the first waveguide layer, the layer thickness of the active layer, and the layer thickness of the second waveguide layer, and $\Delta n$ is a maximum of the refractive index difference between the first waveguide layer and the first cladding layer and the refractive index difference between the second waveguide layer and the second cladding layer, and
(ii) the semiconductor component comprises a ridge waveguide with an effective index step $\Delta neff > 0.1$.

2. The semiconductor component according to claim 1, wherein:
the first waveguide layer, the active layer and the second waveguide layer are designed such that the ratio between the layer thickness of the second waveguide layer on the one hand and the sum total of the layer thickness of the first waveguide layer, the layer thickness of the active layer, and the layer thickness of the second waveguide layer on the other is greater than 0.65.

3. The semiconductor component according to claim 1, wherein:
the first cladding layer, the first waveguide layer, the second waveguide layer, and the second cladding layer are designed such that the condition $\Delta n > 0.15$ is met.

4. The semiconductor component according to claim 3, wherein:
the first cladding layer, the first waveguide layer, the second waveguide layer, and the second cladding layer are designed such that the condition $\Delta n > 0.30$ is met.

5. The semiconductor component according to claim 1, wherein:
the first waveguide layer, the active layer, and the second waveguide layer are designed such that the condition 0.01 μm≤dwL≤0.75 μm is met.

6. The semiconductor component according to claim 5, wherein:
the first waveguide layer, the active layer, and the second waveguide layer are designed such that the condition 0.01 μm≤dwL≤0.5 μm is met.

7. The semiconductor component according to claim 1, wherein:
the active layer extends across the entire region between the reflection facet and the emission facet, wherein the active layer is in direct contact with the reflection facet and the emission facet.

8. The semiconductor component according to claim 1, wherein:
the first waveguide layer, the active layer and the second waveguide layer are designed such that the ratio between the layer thickness of the second waveguide layer on the one hand and the sum total of the layer thickness of the first waveguide layer, the layer thickness of the active layer, and the layer thickness of the second waveguide layer on the other is greater than 0.85.

9. The semiconductor component according to claim 1, wherein:
the ridge waveguide is formed by grooves that are introduced into the second waveguide layer and the second cladding layer, wherein the depth of the grooves is such that a minimum distance between the side of the active layer facing the second waveguide layer and the side of the grooves facing the active layer is greater than 100 nm.

10. The semiconductor component according to claim 9, wherein:
a maximum distance between the side of the active layer facing the second waveguide layer and the side of the grooves facing the active layer is smaller than 500 nm.

11. The semiconductor component according to claim 10, wherein:
a maximum distance between the side of the active layer facing the second waveguide layer and the side of the grooves facing the active layer is smaller than 250 nm.

12. The semiconductor component according to claim 1, wherein:
the ridge waveguide is less than 20 μm in width, preferably less than 10 μm.

13. The semiconductor component according to claim 1, wherein:
the first cladding layer and the first waveguide layer are n-type, the second waveguide layer and the second cladding layer are p-type.

14. The semiconductor component according to claim 1, wherein:
the component comprises neither a diffuser nor a concave lens.

* * * * *